United States Patent [19]

Kramer

[11] Patent Number: 4,681,859

[45] Date of Patent: Jul. 21, 1987

[54] FLUORESCENCE POLARIZATION IMMUNOASSAY FOR HEAVY ANTIGENS

[75] Inventor: Peter B. Kramer, Newton Centre, Mass.

[73] Assignee: Ortho Diagnostic Systems Inc., Raritan, N.J.

[21] Appl. No.: 653,382

[22] Filed: Sep. 21, 1984

[51] Int. Cl.⁴ ............... G01N 33/566; G01N 33/563; G01N 33/536; G01N 33/533
[52] U.S. Cl. .................................... 436/501; 935/76; 935/81; 935/88; 436/512; 436/536; 436/537; 436/546; 436/800
[58] Field of Search ............... 436/546, 501, 512, 537, 436/536, 800; 935/76, 81, 88

[56] References Cited

U.S. PATENT DOCUMENTS

| | | | |
|---|---|---|---|
| 3,939,350 | 2/1976 | Kronick et al. | 250/365 |
| 4,420,568 | 12/1983 | Wang et al. | 436/536 |
| 4,476,228 | 11/1984 | Huchzermeier et al. | 436/500 |

FOREIGN PATENT DOCUMENTS

WO81/01883  7/1981  PCT Int'l Appl.

*Primary Examiner*—Christine M. Nucker
*Assistant Examiner*—Patricia L. DeSantis
*Attorney, Agent, or Firm*—Mark A. Hofer

[57] ABSTRACT

Methods for determining the presence of large molecular weight aqueous ligands. The sample ligands are made to compete with user supplied fluorescently labeled peptides for binding sites on a ligand binding partner. Presence of aqueous ligand and binding of ligand binding partner thereto leaves the fluorescently labeled peptides free to exhibit fluorescence depolarization effects.

2 Claims, No Drawings

FLUORESCENCE POLARIZATION IMMUNOASSAY FOR HEAVY ANTIGENS

FIELD OF THE INVENTION

This invention relates to methods for detecting antigens or other such materials in aqueous samples and in particular, provides for the detection of large molecular weight antigens based upon the principles of fluorescence polarization.

BACKGROUND OF THE INVENTION

The detection of specified antigens (defined as a substance whose introduction into an animal stimulates the production of antibodies capable of reacting specifically therewith), haptens (a substance requiring additional accessory materials before its introduction into an animal stimulates the production of antibodies specific therefor), and the like substances (hereinafter collectively referred to as ligands) in body fluids such as blood, sputum, urine and the like has in recent years become of utmost importance in both the research and clinical environments. The detection of ligands, particularly antigens or antibodies capable of specifically combining therewith (hereinafter collectively termed "anti-ligands" or "ligand binding partner" which terms are also meant to include antibody fragments such as F(ab), F(ab)' etc.) can often be related to various disease states and consequently is extremely useful in diagnosis, in gaining basic understandings concerning the genesis of disease, and in monitoring the effectiveness of therapies therefor. Many schemes for detecting ligands or anit-ligands have evolved over recent years based on the selective, immunological reactivity which characterizes these substances. Generally, these schemes are collectively termed immunoassays.

This invention is particularly concerned with the class of immunoassays which measure changes in fluorescence polarization and depolarization (hereinafter simply referred to as fluorescence depolarization or fluorescence polarization since each refers to the same process but from different viewpoints) for the detection of ligands. In particular, the fluorescence depolarization methods have been most popularly utilized in connection with drug monitoring.

To date, however, fluorescence depolarization has been substantially limited to monitoring antigens or ligands of small molecular weight. Such low molecular weight ligands, on the order of less than 1000 daltons, rotate rapidly in solution. Accordingly, when a small fluorescent molecule is attached to the light antigen or ligand, it also rotates rapidly. Thus, when the fluorescent molecule is excited by polarized light, the resultant fluorescent light radiated by the fluorescent molecule becomes partially depolarized due to the rapid rotation of the fluorescent molecule-ligand. The speed of rotation, and concomitantly the amount of depolarization, dramatically decreases when the low molecular weight ligand becomes substantially heavier such as when it becomes bound to a comparatively much larger antibody (i.e., anti-ligand) molecule. Similarly, limited depolarization is observed when the fluorescent molecule itself is bound to a high molecular weight molecule (e.g., over 1000 daltons). The amount of depolarization as a function of molecular weight (determined by whether an anti-ligand binds to a ligand) can thus serve as the basis for an immunoassay for low molecular weight ligands.

In such a fluorescence depolarization immunoassay, the observation of a decrease in depolarization (e.g., the maintenance of polarization) indicates increased binding of anti-ligand to the fluorescently labeled ligand since such a binding results in a larger molecule which rotates slowly and is thus a less effective depolarizing agent. If, on the other hand, the sample contains ligands which compete with the fluorescently labeled ligands for binding sites on the anti-ligand, then fewer anti-ligand molecules are available to bind to the fluorescently labeled ligands and an increasing level of depolarization is observed. As may be readily appreciated, quantitation of such an assay may be conveniently accomplished using standard preparations for comparison with samples containing unknown levels of the low molecular weight ligand. In fact, this technique is currently being employed by Abbott in their commercially available TDX instrument such as is described in U.S. Pat. No. 4,269,511 and U.S. Pat. No. 4,420,568.

The latter patent, to Wang et al., describes fluorescent depolarization immunoassays utilizing substituted Triazinylaminofluoresceins. A review of this patent, however, highlights the limitations of the fluorescent depolarization techniques to ligands of low molecular weight, generally in the range of 50–4000 and most preferably those within a range of 100–2000. Many investigators have heretofore, however, regarded the practical upper limit as being somewhat lower than those of Wang, more on the order of approximately 1000. As previously described, these limits exist because as the ligands become significantly larger, they no longer rotate rapidly. Consequently, the attached fluorescent molecule also does not rotate rapidly. As a result, little or no depolarization can be observed even before an anti-ligand binds the large molecular weight ligand. In addition, the large molecular weight ligands are no longer significantly affected from a percentage change in weight viewpoint by the binding of an anti-ligand, and thus, they show little increased depolarization when subsequently bound to an anti-ligand. Consequently, the sensitivity of the polarization assay for a ligand rapidly drops off with increasing molecular weight of the ligand.

It is an object of the present invention to remove these limitations by providing methods for detecting the presence of large molecular weight ligands while still employing the principles of fluorescence polarization.

It is yet another object of the present invention to provide methods suitable for all types of ligands regardless of weight, not just the low molecular weight protein free haptens which the Wang et al. U.S. Pat. No. 4,420,568 describes.

SUMMARY OF THE INVENTION

In accordance with the principles and objects of the present invention, there are provided methods for detecting large molecular weight ligands utilizing the principles of fluorescence polarization. These methods entail the competition between the large molecular weight ligand in the aqueous sample for the binding site on an anti-ligand receptor with a user supplied reagent comprising fluorescently labeled, binding site simulator means. In the most preferred embodiment, the binding site simulator means will comprise a peptide. The ideal peptide is produced in accordance with its ability to immunologically simulate the antigenic determinant or binding site present on the large molecular weight ligand to which the anti-ligand binds. Thus, presence of the sample ligand results in binding of the anti-ligand thereto thereby reducing the amount of anti-ligand available to combine with the fluorescently labeled peptide. Free, fluorescently labeled peptide exhibits fluorescence depolarization while fluorescently labeled peptide bound to anti-ligand exhibits detectably less fluorescence depolarization.

DETAILED DESCRIPTION OF THE INVENTION AND BEST MODE

Since 1975 and the Kohler and Milstein article appearing in Nature 256: 495–497 describing the generation of hybridomas and the resultant production of monoclonal antibodies, much progress has been made in selecting, identifying, and understanding antigenic determinants. In general the term antigenic determinants is used to refer to those regions of the antigen or ligand which are intimately involved in immunological reaction with anti-ligands. In essence, it is these determinants which differentiate antigens and therefore antibodies from one another on the basis of immunological specificity. Additionally, concurrent advances in the art of organic chemical manipulations have permitted the isolation and purificaton of such antigenic determinants from antigens in general. Verification and identification of various antigenic determinants may, of course, be easily accomplished by competitive binding analysis using the complete antigen and the respective antibody.

The molecular makeup of the antigenic determinant can be suitably analyzed utilizing standard high performance liquid chromatography (HPLC) and other protein sequencing techniques. Useful references for such procedures include Receptor Binding and Antigenic Domains of Gonoccocal Pili, Schoolnik et al, Microbiology—1982, Schlessinger, A.S.M., p. 312–316.

Once the amino acid order of a particular antigenic determinant is known, readily available peptide synthesizers such as those available from Beckman or Applied Biosystems, can be utilized to produce synthetic peptides capable of emulating the binding site of the large ligand. It, of course, is naturally to be understood that the methods of the instant invention are not limited to large ligands and may be equally employed with any size ligand. Further, non-proteinaceous antigenic determinants can be equally well simulated, the major differences being the substitution of suitable techniques for chemical characterization of the site to the extent necessary in order to recreate the site with a binding site simulator means such as a low molecular weight molecule.

Choice of the fluorescent molecule for labeling is advantageously flexible and is largely up to the preferences of the practitioner, there being a great variety of fluorescent labels commercially available at very low cost. It will be readily appreciated that the fluorescent labels are ideally chosen in accordance with their size; the smaller the molecule, the more rapid it can rotate, and the more effective it is as a depolarizer. Similarly, the methods employed in conventional immunoassays for coupling fluorescent labels to biologically active molecules such as ligands, anti-ligands, or other molecules are also well-known and accordingly need not be reviewed here.

Synthesis of the determinant by peptide generation or other chemical process are not the only ways the instant invention may be practiced. Other alternative methods may be more advantageous to the individual practitioner based upon his or her expertise, the materials available, and the type of determinant to be simulated. For instance, the recombinant DNA techniques now becoming well-known may be employed to reconstruct the small portion of the antigen critical to binding and any additional structures to aid in attaching a fluorescent molecule or the fluorescent molecule itself. Such methods would entail identification of the encoding DNA. The identified DNA sequence is then isolated or synthesized, inserted into suitable carriers such as plasmids and the like, transfected into suitable cells such as bacteria (e.g., *Escherichia coli* pursuant to the methods of Cohen and Boyer described in U.S. Pat. No. 4,237,224 or into eucaryotic cells such as by the methods of Axel et al. in U.S. Pat. No. 4,399,216) for the production of large amounts of the protein serving as the antigenic determinant. The relevant procedures for isolation and purification of products from transfected cells are also processes well-known. A useful reference in this regard is Maniates et al., Molecular Cloning: A Laboratory Manual, Cold Spring Harbor, New York (1982) which provides numerous "recipes" and material sources for practicing DNA recombinant techniques and plasmid construction. Other useful references include Maniates, Isolation of Structural Genes from Libraries of Eucoryotic DNA, Cell 15: 687–701 (1978) and *Recombinant DNA*, Ed. by Wu et al., Academic Press, New York (1983).

Selection of the critical determinant portions may be alternately accomplished by "mincing" the ligand into smaller pieces such as by mechanical means (sonication) or chemical means (digestion, etc.) and filtering the resultant material through an affinity chromatography column having immobilized thereon suitable antibody to which the antigenic determinant portions become attached. Thereafter, the determinant portions may be eluted from the column with suitable solvents in well-known procedures such as by pH alteration. This isolation and purification method can, of course, also be used in combination with the previously described DNA techniques.

It will be readily appreciated by those skilled in the art that numerous modifications to the foregoing may be made, particularly with regard to the identification, isolation or synthesis of the antigenic site simulator, without departing from either the spirit or scope of the present invention.

What is claimed is:

1. A method for determining the presence of a ligand in an aqueous sample comprising the steps of:

providing a ligand binding partner capable of specifically combining with said sample ligand at a binding site on said ligand;

further providing fluorescently labeled epitope simulating peptide capable of specifically combining with said ligand binding partner whereby binding of (i) said sample ligand of (ii) said simulating peptide to said ligand binding partner blocks binding of (i) said simulating peptide or (ii) said sample ligand, respectively, to said ligand binding partner;

allowing said sample ligand and said simulating peptide to combine with said ligand binding partner;

illuminating said fluorescent label with polarized light; and detecting fluorescence depolarization and relating said depolarization to the presence or absence of ligand in said sample.

2. In a method for detecting the presence of a ligand in an aqueous sample based upon its competition with a fluorescently labeled ligand for the binding site on an anti-ligand partner capable of specifically reacting with either sample ligand or labeled ligand and detecting the resultant differences in fluorescent depolarization and correlating said differences with the presence of ligand in said aqueous sample, the improvement comprising providing a fluorescently labeled epitope simulating peptide for simulating the region of the sample ligand which binds to the anti-ligand whereby the presence of ligands, with a molecular weight in excess of about 1000 daltons in an aqueous sample can be determined.

* * * * *